US007949094B2

(12) United States Patent
Ahn

(10) Patent No.: US 7,949,094 B2
(45) Date of Patent: May 24, 2011

(54) RAIL SYSTEM AND X-RAY IMAGING APPARATUS USING THE SAME

(75) Inventor: Pan Soon Ahn, Gunpo-si (KR)

(73) Assignee: Medien International Co., Ltd., Gunpo-si (KR)

( * ) Notice: Subject to any disclaimer, the term of this patent is extended or adjusted under 35 U.S.C. 154(b) by 0 days.

(21) Appl. No.: 12/478,462

(22) Filed: Jun. 4, 2009

(65) Prior Publication Data

US 2010/0232574 A1    Sep. 16, 2010

(30) Foreign Application Priority Data

Mar. 10, 2009  (KR) ................. 10-2009-0020278

(51) Int. Cl.
*G01N 23/04* (2006.01)
(52) U.S. Cl. ......................... 378/57; 378/197
(58) Field of Classification Search .............. 378/193, 378/196, 197, 198, 189, 57
See application file for complete search history.

(56) References Cited

U.S. PATENT DOCUMENTS

| 6,234,671 | B1 | 5/2001 | Solomon et al. |
| 6,733,176 | B2 | 5/2004 | Schmitt |
| 2007/0140435 | A1* | 6/2007 | Schwieker ............. 378/193 |

* cited by examiner

*Primary Examiner* — Hoon Song
(74) *Attorney, Agent, or Firm* — Fredrikson & Byron, P.A.

(57) ABSTRACT

Disclosed herein are a rail system and an X-ray imaging apparatus using the same. The rail system includes a rail unit, a detecting unit and an X-ray generating unit. The rail unit is provided on a support surface and extends for a predetermined length. The detecting unit is provided on the rail unit and includes a detector stand which is provided on the rail unit so as to be movable in the longitudinal direction of the rail unit, a detector arm which has a bent structure and is provided on a side surface of the detector stand so as to be movable upwards and downwards, and a detector which is rotatably coupled to the detector arm. The X-ray generating unit is provided on the rail unit at a position facing the detector and includes a tube stand which is provided on the rail unit so as to be movable in the longitudinal direction of the rail unit, a tube arm which is provided on the tube stand so as to be movable upwards and downwards, an X-ray tube which is coupled to the tube arm so as to be rotatable with respect to the tube arm, and a collimator which is fastened to the X-ray tube.

4 Claims, 10 Drawing Sheets

RAIL SYSTEM AND X-RAY IMAGING APPARATUS USING THE SAME

This patent application claims the benefit of priority under 35 U.S.C. §119 from Korean Patent Application No. 10-2009-0020278 filed on Mar. 10, 2009, the contents of which are incorporated herein by reference.

BACKGROUND OF THE INVENTION

1. Field of the Invention

The present invention relates generally to rail systems and X-ray imaging apparatuses using the same and, more particularly, to a rail system for medical X-ray imaging apparatuses which are used in hospitals in order to image patient's bodies, and an X-ray imaging apparatus using the rail system.

2. Description of the Related Art

As is well known to those skilled in the art, when high-speed electrons strike a solid target, electromagnetic waves having high penetration are produced. These electromagnetic waves are called X-rays.

The discovery of the X-ray having deep penetration made it possible to observe the interior of a human body without opening up the body, thus greatly contributing to the development of medical science.

That is, before the discovery of the X-ray, conditions of internal organs or bones of a human body could not be observed simply from the outward appearance. Therefore, when the human body showed abnormal symptoms, the human body had to be opened up to determine with the naked eye whether it was normal or not.

Since discovery of the X-ray by Roentgen and its use in the medical profession, whether a patient's body is normal or not can be determined by X-ray imaging without the opening up of the body as was conducted before the discovery of the X-ray. Hence, it became easy to conduct medical treatment or examination of the patient.

However, in the conventional art, when installing a medical X-ray imaging apparatus, there is a spatial limitation. In detail, to date, in the case of the conventional rail system which has been generally used, a rail along which a tube stand moves is provided under a ceiling, and a detector is installed below the rail. In this case, several detectors may be provided, so that the apparatus can be used in various positions. However, there is a disadvantageous in that the height of the ceiling must range between from 2700 mm to 2800 mm. Furthermore, the installation of the tube stand under the ceiling requires separate rail installation work that must tear off the ceiling. The work of installing the tube stand on the rail provided under the ceiling increases the installation cost. As well, in the case of medium and small hospitals having relatively small spaces, installation of the X-ray imaging apparatus may be impossible.

Meanwhile, in the case of a structure in which a detector is perpendicularly connected to a detector stand, in order to set the detector and an X-ray generating unit such that the centers thereof are exactly aligned with each other to generate an image correctly, a tube stand must be disposed right above the upper end of the detector stand. Therefore, in the same manner as the structure in which the rail is provided under the ceiling, the ceiling of an installation room must be more than 2700 mm high. In addition, in this structure, the X-ray imaging apparatus cannot be implemented by using a single rail, and at least two rails are necessary. This increases the installation cost. Moreover, because two or more rails are provided on opposite sides of a table on which a patient lies for X-ray imaging, there is a problem in that movement of the table is greatly limited.

SUMMARY OF THE INVENTION

Accordingly, the present invention has been made keeping in mind the above problems occurring in the prior art, and an object of the present invention is to provide a rail system for X-ray imaging apparatuses which can reduce installation space and thus increase space available for movement of a table on which a patient is lying for X-ray imaging, and an X-ray imaging apparatus using the rail system.

In order to accomplish the above object, the present invention provides a rail system for X-ray imaging apparatuses and an X-ray imaging apparatus using the rail system. The rail system includes: a rail unit provided on a support surface and extending a predetermined length in a longitudinal direction; a detecting unit provided on the rail unit, and an X-ray generating unit provided on the rail unit at a position facing the detector the detecting unit. The detecting unit has a detector stand provided on the rail unit so as to be movable in the longitudinal direction of the rail unit, a detector arm coupled to a side surface of the detector stand so as to be movable upwards and downwards, the detector arm having a bent structure, and a detector coupled to the detector arm, the detector being rotatable with respect to the detector arm. The X-ray generating unit has a tube stand provided on the rail unit so as to be movable in the longitudinal direction of the rail unit, a tube arm provided on the tube stand so as to be movable upwards and downwards, an X-ray tube coupled to the tube arm so as to be rotatable with respect to the tube arm, and a collimator fastened to the X-ray tube.

The rail unit may include: a rail supported on the support surface and extending a predetermined length; a rail guide provided along an entire length of the rail; and a rack gear provided along the entire length of the rail.

The detecting unit may include: a detector support plate having under a lower surface thereof a guide block movably fitted over the rail guide; a detector stand moving motor provided on the detector support plate to provide drive force for moving the detector support plate with respect to the rail in the longitudinal direction of the rail; a pinion gear provided on an output shaft of the detector stand moving motor, the pinion gear engaging with the rack gear of the rail unit; a detector lift motor provided on the detector support plate to provide drive force for moving the detector support plate upwards and downwards; a lower chain pulley coupled to an output shaft of the detector lift motor through a belt; the detector stand placed upright on the detector support plate; a chain engaging with the lower chain pulley, the chain provided to move over an entire range within which the detector moves upwards and downwards; an upper chain pulley provided on an upper end of the detector stand so as to be rotatable, the upper chain pulley engaging with the chain; a detector guide rail mounted to the detector stand, the detector guide rail extending a predetermined length in a vertical direction of the detector stand; an arm assembly coupled on an inner surface thereof to the chain, the arm assembly movably fitted over the detector guide rail; the detector arm fastened to a surface of the arm assembly facing the X-ray generating unit; a detector rotating motor provided on the detector arm; a detector mounting plate coupled to an output shaft of the detector rotating motor through a worm gear engagement structure so as to be rotatable; and the detector fastened to the detector mounting plate, so that the detector is rotatable with respect to the detector arm.

The X-ray generating unit may include: a tube stand support plate having under a lower surface thereof a guide block movably fitted over the rail guide; a tube stand moving motor provided on the tube stand support plate to provide drive force for moving the tube stand support plate with respect to the rail in the longitudinal direction of the rail; a pinion gear provided on an output shaft of the tube stand moving motor, the pinion gear engaging with the rack gear of the rail unit; the tube stand placed upright on the tube stand support plate; a tube lift motor provided in an upper end of the tube stand; a pulley shaft connected to an output shaft of the tube lift motor by a belt, so that the pulley shaft is rotated by rotation of the output shaft of the lift motor; a pulley fitted over the pulley shaft; a tube stand wire provided in the tube stand, the tube stand wire being connected to the pulley; a tube guide rail mounted to the tube stand, the tube guide rail extending a predetermined length in a vertical direction of the tube stand; the tube arm movably coupled to the tube guide rail, the tube arm being connected to the tube stand wire so that the tube arm is moved upwards and downwards by movement of the tube stand wire; a tube rotating motor provided on a distal end of the tube arm; a rotating plate fastened to an output shaft of the tube rotating motor; the X-ray tube coupled to the rotating plate, so that the X-ray tube is rotated along with the rotating plate; and the collimator fastened to the X-ray tube to control an X-ray radiation dispersal range.

Furthermore, the detector stand may further include a table fastener.

In order to accomplish the above object, the present invention provides a rail system for X-ray imaging apparatuses and an X-ray imaging apparatus using the rail system. The rail system includes: a rail unit provided on a support surface and extending a predetermined length in a longitudinal direction; a detecting unit provided on the rail unit, the detecting unit having a detector stand provided on the rail unit so as to be movable in the longitudinal direction of the rail unit, a detector arm provided on a front surface of the detector stand so as to be movable upwards and downwards, and a detector coupled to the detector arm so as to be rotatable with respect to the detector arm; and an X-ray generating unit provided on the rail unit, the X-ray generating unit having a tube stand provided on the rail unit so as to be movable in the longitudinal direction of the rail unit, a tube arm coupled to the tube stand so as to be movable upwards and downwards such that a distal end of the tube arm faces the detecting unit, the tube arm having a bent structure, an X-ray tube coupled to a front surface of the tube arm so as to be rotatable with respect to the tube arm, and a collimator fastened to the X-ray tube.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
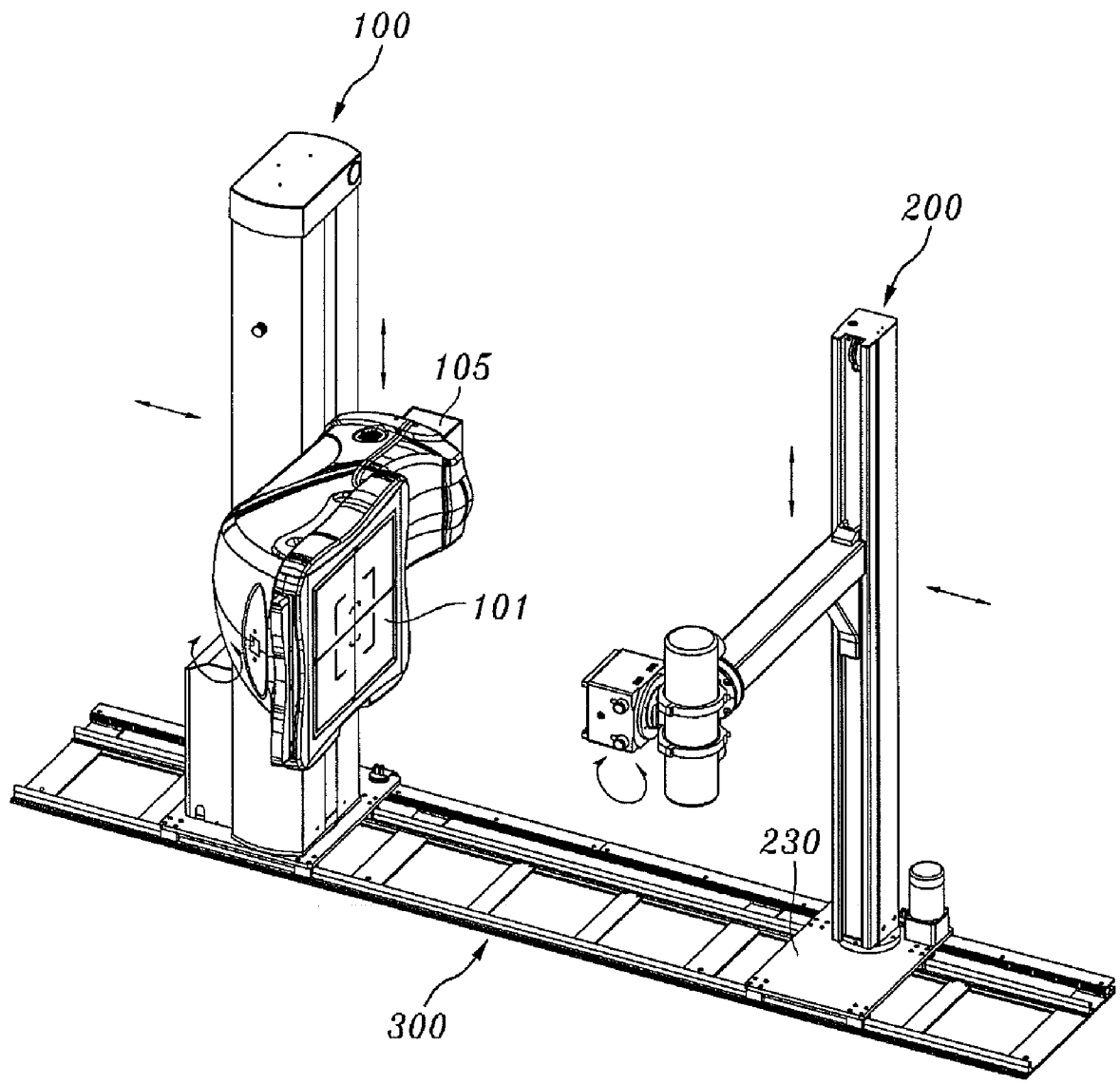
FIG. 1 is a perspective view illustrating a rail system, provided with a detector arm having a bent structure, and an X-ray imaging apparatus using the rail system, according to a first embodiment of the present invention.

Hereinafter, a preferred embodiment of the present invention will be described in detail with reference to the attached drawings. Reference now should be made to the drawings, in which the same reference numerals are used throughout the different drawings to designate the same or similar components. In the following description, when it is determined that the detailed description for the conventional function and conventional structure confuses the gist of the present invention, the description may be omitted.

A rail system and an X-ray imaging apparatus using the rail system according to the present invention is characterized in that a detector and an X-ray generating unit are provided on a rail so as to be movable along the rail so that installation space of a table on which a patient is seated can be sufficiently ensured. Furthermore, the X-ray imaging apparatus of the present invention can be installed even in space having a relatively low floor height. In addition, because a table fastener is provided on a detector stand and a table is mounted to the detector stand through the table fastener, a problem which may occur due to movement of the table with respect to a detector can be avoided when imaging.

FIG. 1 is a perspective view illustrating a rail system, provided with a detector arm having a bent structure, and an X-ray imaging apparatus using the rail system, according to a first embodiment of the present invention.

Figure 2:
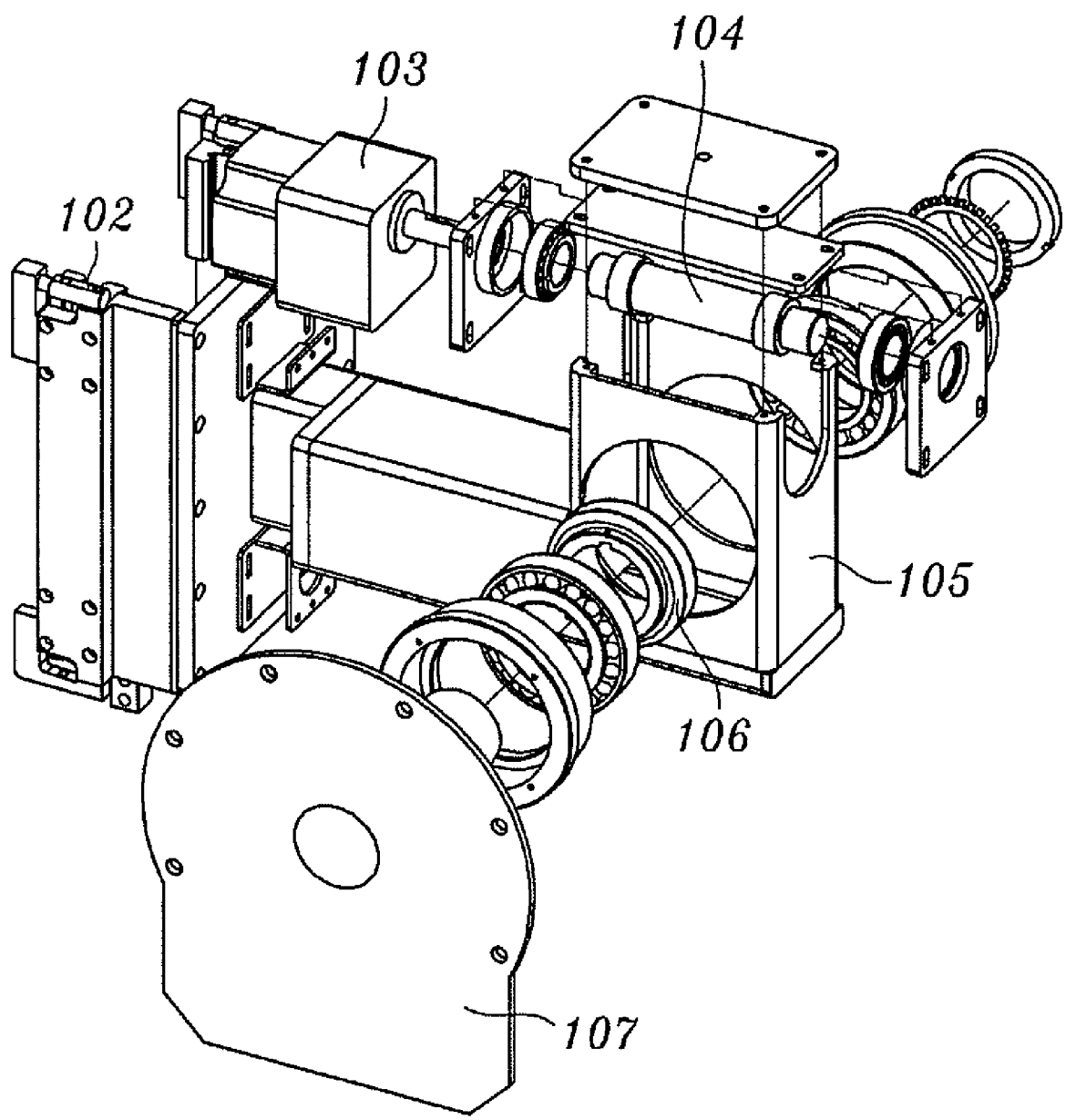
FIG. 2 is an exploded perspective view showing the detector arm of the rail system according to the first embodiment of the present invention.

FIG. 2 is an exploded perspective view showing the detector arm of the rail system according to the first embodiment of the present invention.

Figure 3:
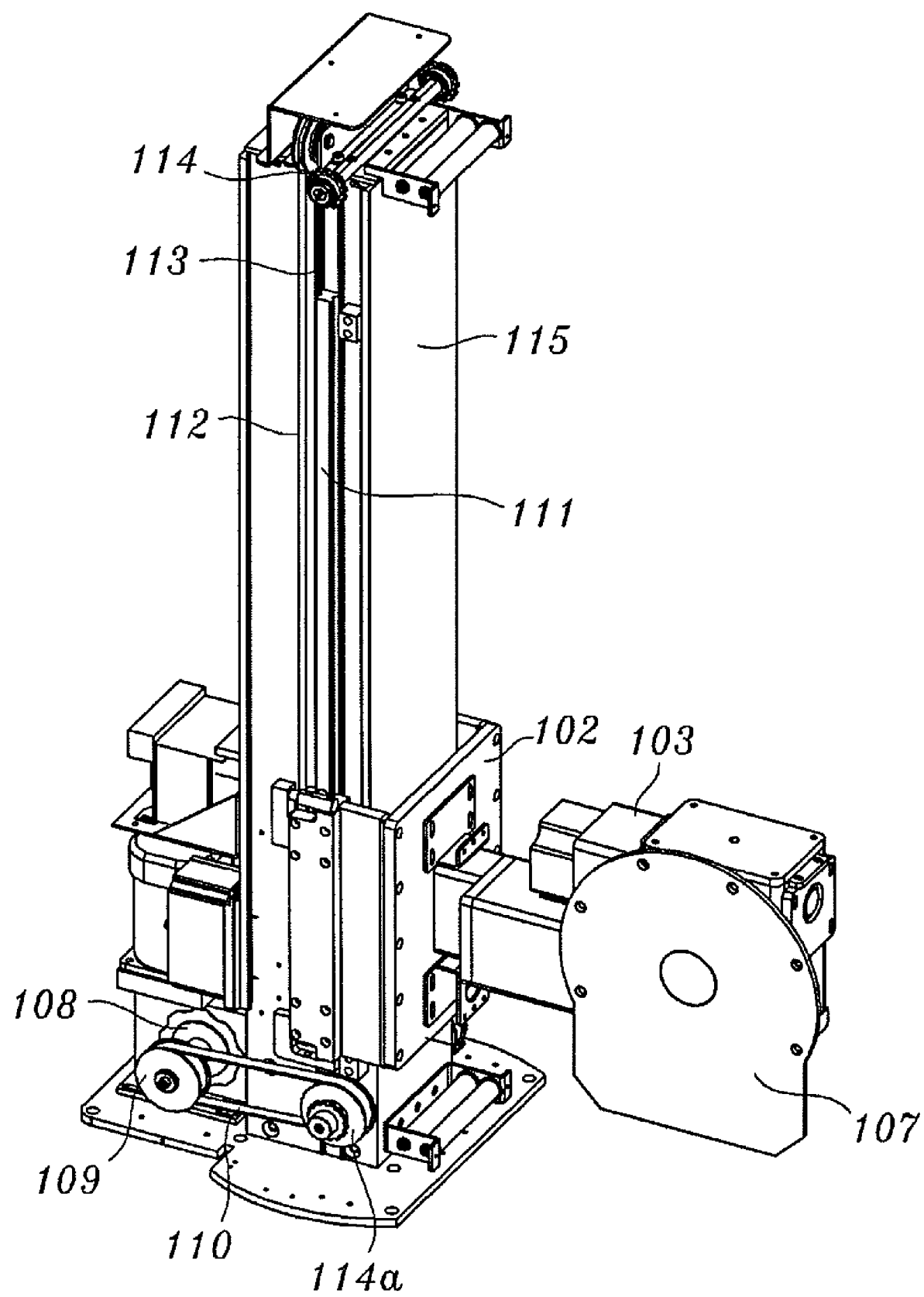
FIG. 3 is a perspective view illustrating a detector stand of the rail system according to the first embodiment of the present invention.

FIG. 3 is a perspective view illustrating a detector stand of the rail system according to the first embodiment of the present invention.

Figure 4:
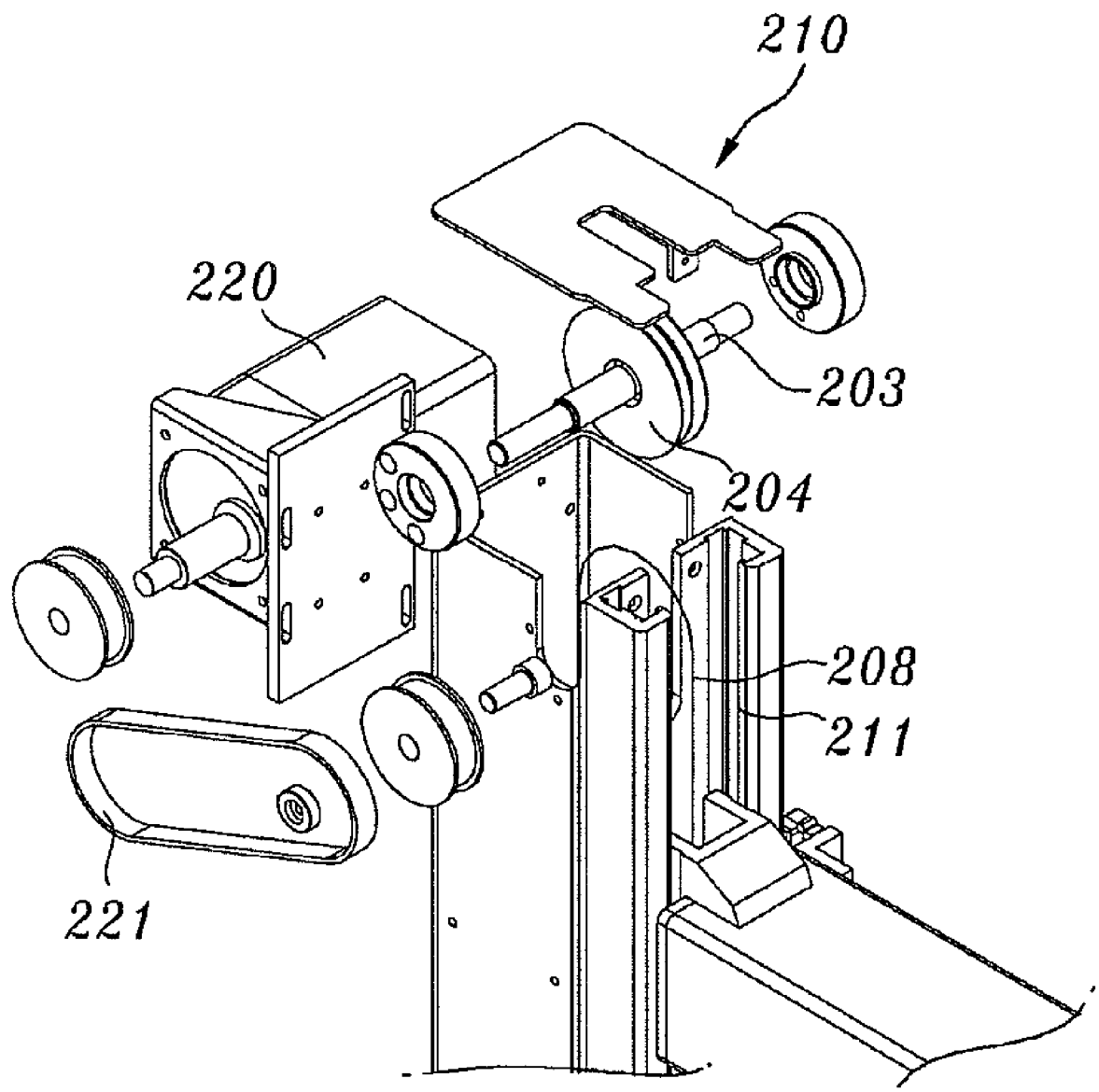
FIG. 4 is an exploded perspective view illustrating a tube stand of the rail system according to the first embodiment of the present invention.

FIG. 4 is an exploded perspective view illustrating a tube stand of the rail system according to the first embodiment of the present invention.

Figure 5:
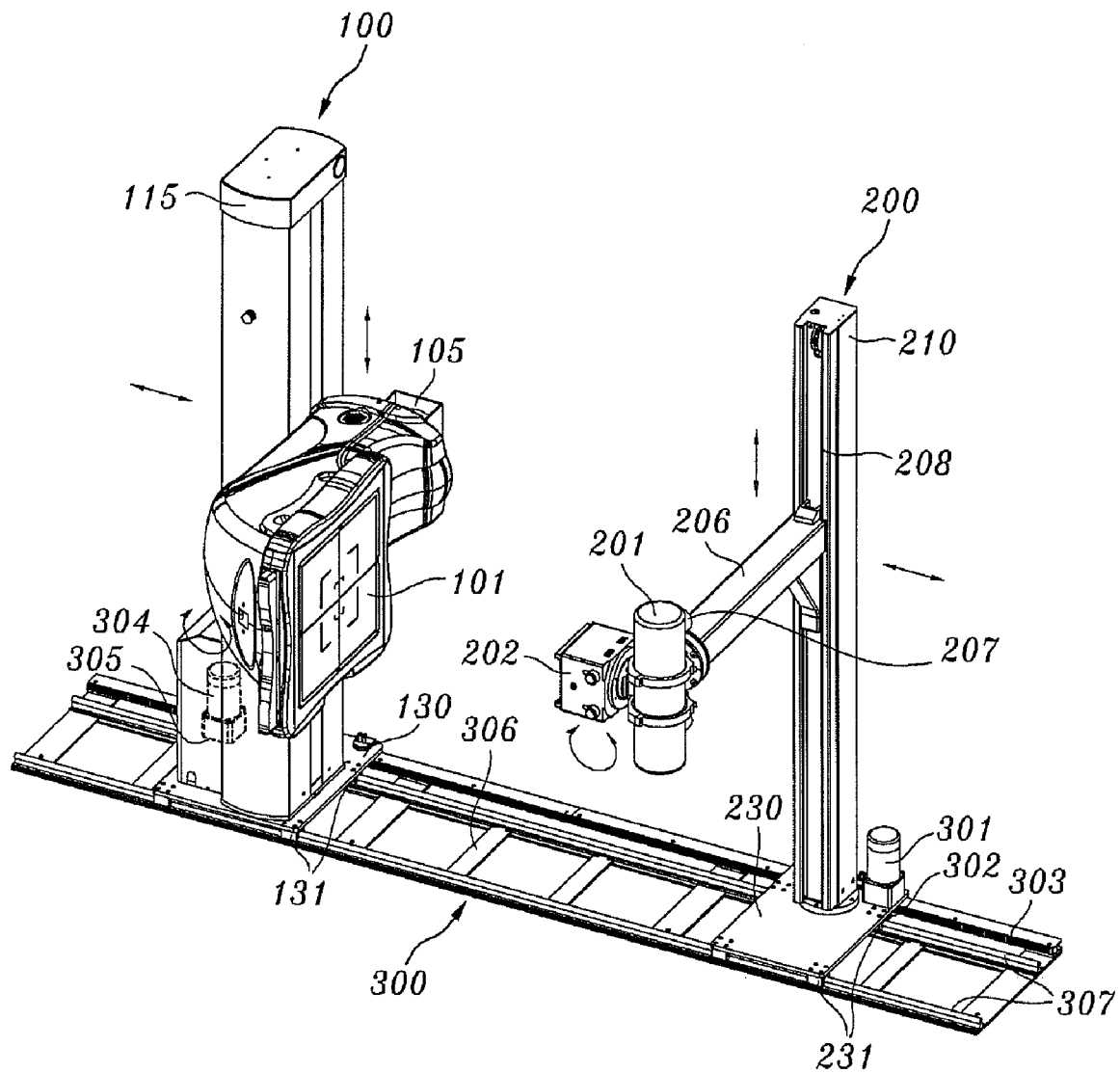
FIG. 5 is a perspective view illustrating a method of moving the X-ray imaging apparatus along the rail system according to the first embodiment of the present invention.

FIG. 5 is a perspective view illustrating a method of moving the X-ray imaging apparatus along the rail system according to the first embodiment of the present invention.

Figure 6:
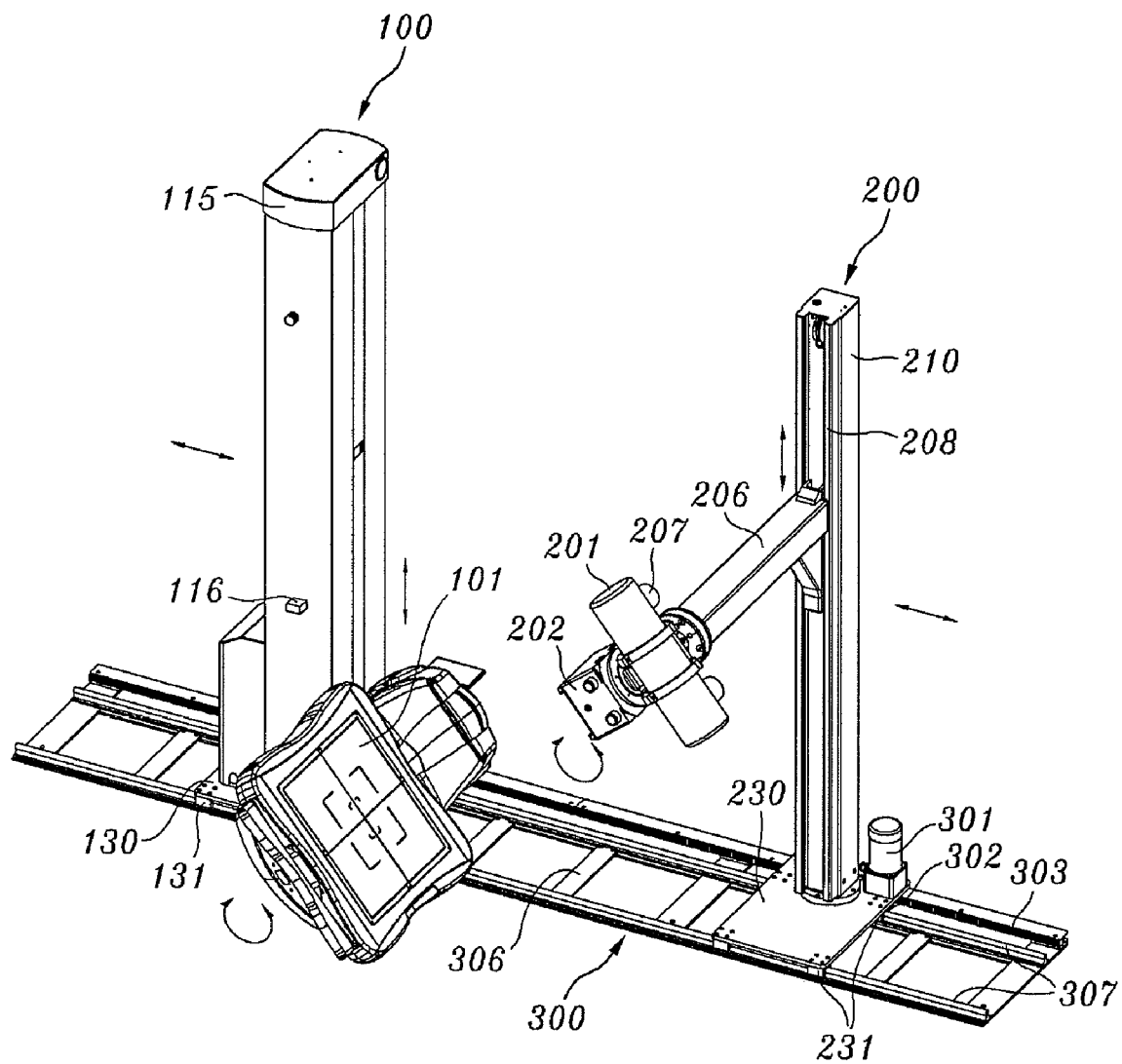
FIG. 6 is a perspective view showing the operation of the X-ray imaging apparatus according to the first embodiment of the present invention when imaging a patient who is in an inclined state.

FIG. 6 is a perspective view showing the operation of the X-ray imaging apparatus according to the first embodiment of the present invention when imaging a patient who is in an inclined state.

Figure 7:
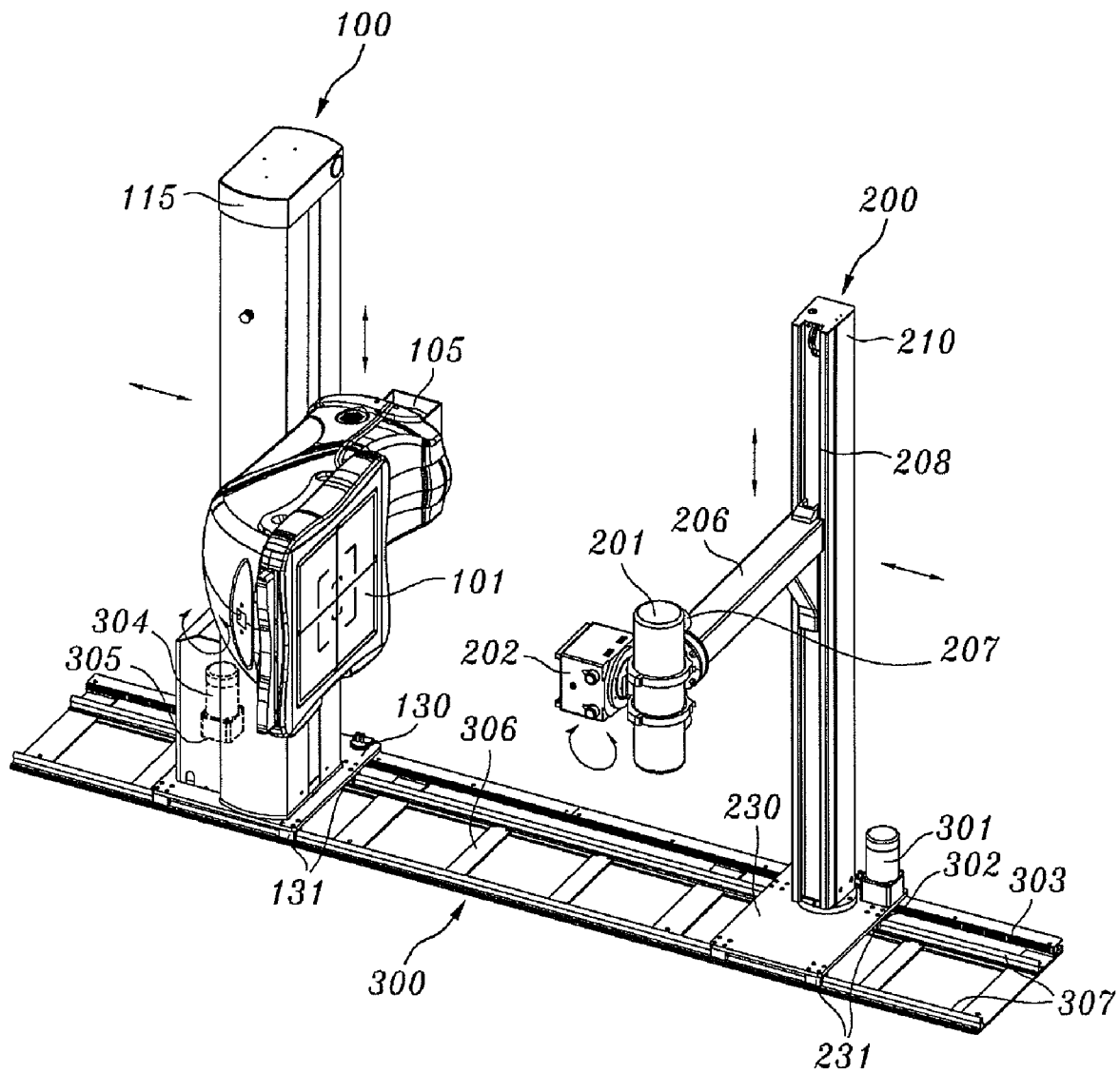
FIG. 7 is a perspective view showing the operation of the rail system and the X-ray imaging apparatus which are in chest imaging mode according to the first embodiment of the present invention.

FIG. 7 is a perspective view showing the operation of the rail system and the X-ray imaging apparatus which are in a chest imaging mode according to the first embodiment of the present invention.

Figure 8:
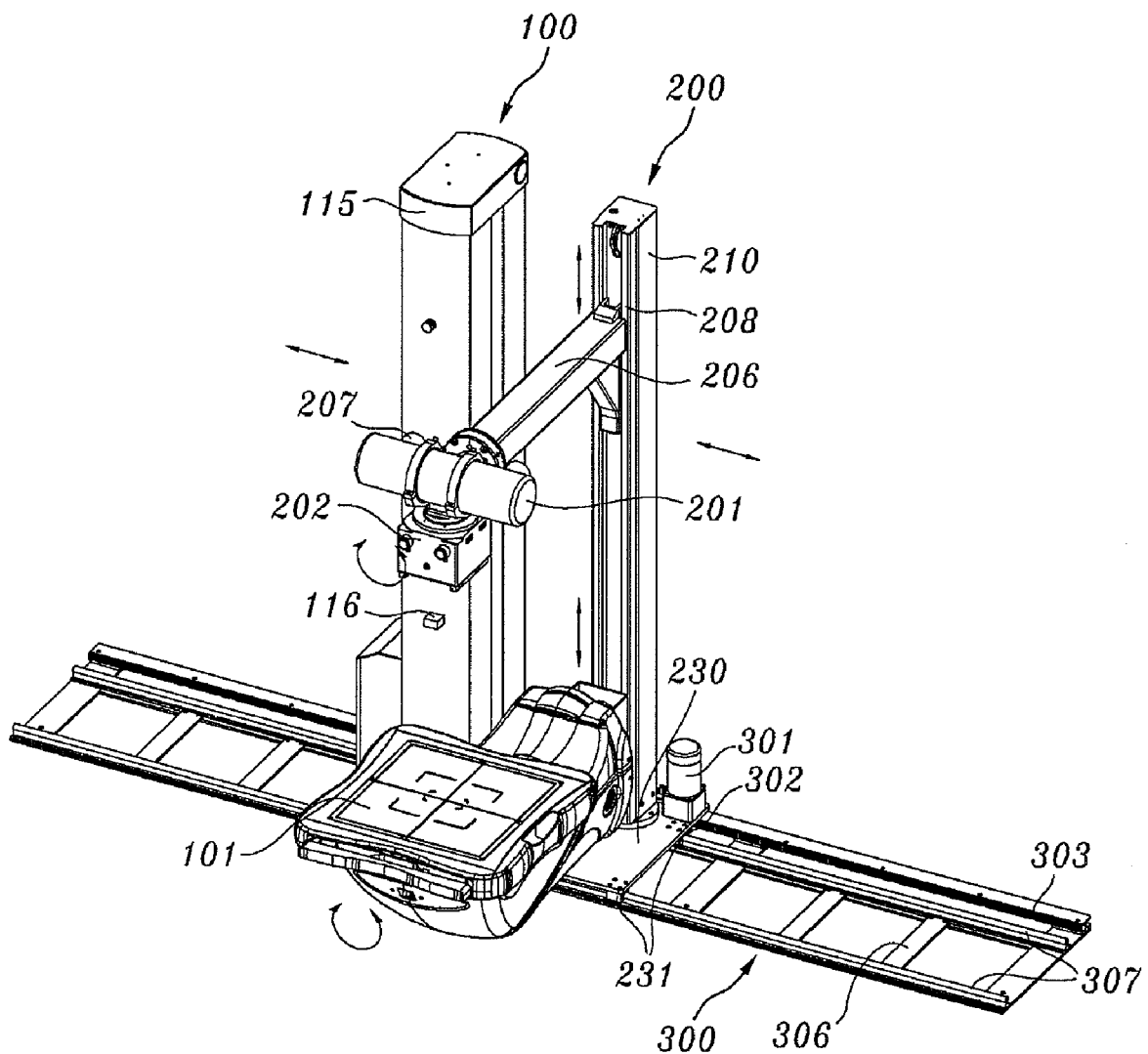
FIG. 8 is a perspective view showing the operation of the rail system and the X-ray imaging apparatus which are in table mode according to the first embodiment of the present invention.

FIG. 8 is a perspective view showing the operation of the rail system and the X-ray imaging apparatus which are in table mode according to the first embodiment of the present invention.

As shown in FIGS. 1 through 8, the rail system and the X-ray imaging apparatus using the rail system according to the first embodiment of the present invention include a rail unit 300, a detecting unit 100 and an X-ray generating unit 200. The rail unit 300 includes a rail 306, rail guides 307 and a rack gear 303. The detecting unit 100 includes a detector support plate 130, a detector stand moving motor 304, a pinion gear 305, a detector lift motor 108, a lower chain pulley 114a, a detector stand 115, a chain 113, an upper chain pulley 114, a detector guide rail 111, an arm assembly 102, a detector arm 105, a detector rotating motor 103, a detector mounting plate 107 and a detector 101. The X-ray generating unit 200 includes a tube stand support plate 230, a tube stand moving motor 301, a pinion gear 302, a tube stand 210, a tube lift motor 220, a pulley shaft 203, a pulley 204, a tube stand wire 208, a tube guide rail 211, a tube arm 206, a tube rotating motor 207, a rotating plate 209, an X-ray tube 201 and a collimator 202.

The coupling relationship and functions of the elements of the rail system and the X-ray imaging apparatus according to the present invention will be explained.

First, the rail unit 300 will be explained in detail below.

The rail 306 extends a predetermined length in a longitudinal direction. Preferably, the rail 306 is fixed to the surface of the support of the place where the X-ray imaging apparatus is installed.

The rail guides 307 are fastened along the entire length of the rail 306. Preferably, the rail guides 307 are provided over the entire range within which the detecting unit 100 and the X-ray generating unit 200 move.

The rack gear 303 is fastened to the entire length of the rail 306. The rack gear 303 engages both with a pinion gear 305 provided on the output shaft of the detector stand moving motor 304 and with a pinion gear 302 provided on the output shaft of the tube stand moving motor 301, such that the detecting unit 100 and the X-ray generating unit 200 can move in the longitudinal direction of the rail unit 300. A method of moving the detecting unit 100 and the X-ray generating unit 200 in the longitudinal direction of the rail unit 300 is not limited to the above-mentioned method. For example, those skilled in the art can easily appreciate that a method using a ball bearing (not shown) and an LM guide (not shown) may be used.

The detecting unit 100 of the present invention will be explained below.

The detector support plate 130 has guide blocks 131 which are movably fitted over the rail guides 307. Because of the coupling of the guide blocks 131 to the rail guides 307, the detector support plate 130 can move in the longitudinal direction of the rail guides 307 within a limited range.

The detector stand moving motor 304 is fastened to the detector support plate 130 and provides drive force with which the detector support plate 130 can move along the fixed rail 306.

The pinion gear 305 is provided on the output shaft of the detector stand moving motor 304 and engages with the rack gear 303.

The detector lift motor 108 is fastened to the detector support plate 130 and provides drive force with which the detector arm 105 can move upwards or downwards.

The lower chain pulley 114a is connected to the output shaft of the detector lift motor 108 through a belt 110.

The detector stand 115 having a predetermined length is placed upright on the detector support plate 130.

The chain 113 engages with the lower chain pulley 114. Preferably, the chain 113 is provided over the entire range within which the detector 101 moves upwards and downwards along the detector stand 115.

The upper chain pulley 114 is rotatably provided in the upper end of the detector stand 115 and engages with the chain 113.

The detector guide rail 111 is mounted to the detector stand 115 and extends a predetermined length in the vertical direction of the upright detector stand 115.

The arm assembly 102 is coupled on the inner surface thereof to the chain 113 and is fitted over the detector guide rail 111.

In the detecting unit 100 having the above-mentioned construction, rotating force generated by rotation of the output shaft of the detector lift motor 108 is transmitted to the lower chain pulley 114a through the belt 110. Then, the chain 113 which engages with the upper chain pulley 114 and the lower chain pulley 114a is rotated by the rotation of the lower chain pulley 114a. As a result, the arm assembly 102 which is fastened to the chain 113 is moved upwards or downwards by the rotation of the chain 113 under the guidance of the detector guide rail 111.

The detector arm 105 is fastened to a surface of the arm assembly 102 corresponding to the right side of the detector stand 115.

The detector rotating motor 103 is fastened to the detector arm 105.

The detector mounting plate 107 is coupled to the output shaft of the detector rotating motor 103 through a worm gear engagement structure so as to be rotatable.

The rotating force of the detector rotating motor 103 is transmitted to the detector mounting plate 107 through the worm gear engagement structure. Thereby, the detector mounting plate 107 rotates with respect to the detector arm 105.

In the rail system and the X-ray imaging apparatus according to the present invention, not only the worm gear engagement structure but also other well-known rotating force transmission structures can be used as the method of transmitting rotating force from the detector rotating motor 103 to the detector mounting plate 107.

The detector 101 is fastened to the detector mounting plate, so that the detector 101 is rotatable with respect to the detector arm 105. The detector 101 receives X-rays, which have been radiated from the X-ray generating unit 200 and have passed through the body of a patient, and sends data obtained from the X-rays to a control unit (not shown).

Below, the X-ray generating unit 200 according to the present invention will be explained.

The tube stand support plate 230 has under the lower surface thereof guide blocks 231 which are movably fitted over the rail guides 307.

The tube stand moving motor 301 is provided on the tube stand support plate 230 to provide drive force for moving the tube stand support plate 230 with respect to the fixed rail 306 in the longitudinal direction of the rail 306.

The pinion gear 302 is provided on the output shaft of the tube stand moving motor 301 and engages with the rack gear 303 of the rail unit 300.

The rotating force of the tube stand moving motor 301 is transmitted to the rack gear 303 through the pinion gear 302 provided on the output shaft of the tube stand moving motor 301. Thereby, the tube stand support plate 230 moves along the rail 306 in the longitudinal direction of the rail 306. Here, the movement of the tube stand support plate 230 along the rail 306 is guided by the rail guides 307 which are coupled to the guide blocks 231 provided under the lower surface of the tube stand support plate 230.

A method of moving the X-ray generating unit 200 in the longitudinal direction of the rail unit 300 is not limited to the above-mentioned method. For example, those skilled in the art will can easily appreciate that a method using a ball bearing (not shown) and an LM guide (not shown) may be used.

The tube stand 210 is placed upright on the tube stand support plate 230.

The tube lift motor 220 is fastened to the upper end of the tube stand 210.

The pulley shaft 203 is connected to the output shaft of the tube lift motor 220 by a belt 221, so that the pulley shaft 203 can be rotated by the operation of the lift motor 220.

The pulley 204 is firmly fitted over the pulley shaft 203.

The tube stand wire 208 is provided in the tube stand 210 and is connected to the pulley 204.

The tube guide rail 211 is mounted to the tube stand 210 and extends a predetermined length in the vertical direction of the upright tube stand 211.

The tube arm 206 is movably coupled to the tube guide rail 211 and is connected to the tube stand wire 208 so that the tube arm 206 is moved upwards and downwards by movement of the tube stand wire 208.

In the X-ray generating unit 200 having the above-mentioned construction, when the tube lift motor 220 rotates, the pulley shaft 203 is also rotated by the rotating force transmitted from the tube lift motor 220 through the belt 221. Then, the tube stand wire 208 is rotated around the pulley shaft 203 by the rotation of the pulley shaft 203, thus moving upwards or downwards, that is, in the vertical direction of the upright tube stand 210.

Thereby, the tube arm 206 which is fastened to the tube stand wire 208 is moved upwards or downwards along the tube stand 210.

An ascending or descending method of the X-ray generating unit 200 is not limited to the above-mentioned method. For example, those skilled in the art easily can see that a method using a ball bearing (not shown) and an LM guide (not shown) may be used.

The tube rotating motor 207 is provided on the distal end of the tube arm 206.

The rotating plate 209 is fastened to the output shaft of the tube rotating motor 207.

The X-ray tube 201 is coupled to the rotating plate 209, so that the X-ray tube 201 is rotated along with the rotating plate 209. The X-ray tube 201 functions to generate X-rays.

The collimator 202 is fastened to the X-ray tube 201 to control an X-ray radiation range.

Because of the above construction, the rotating plate 209 is rotated by the rotating force of the tube rotating motor 207. Thereby, the X-ray tube 201 fastened to the rotating plate 209 rotates.

A method of rotating the X-ray tube 201 is not limited to the above-mentioned method, and any well-known rotating method may be used.

The operation of the rail system and the X-ray imaging apparatus using the rail system according to the present invention will be described below.

As shown in FIG. 6, a distance between the detector stand 115 and the tube stand 210 can be controlled by controlling the rotation of the detector stand moving motor 304 and the tube stand moving motor 301.

The heights of the detector arm 105 and the tube arm 206 can be adjusted by controlling the rotation of the detector lift motor 108 and the tube lift motor 220, respectively.

A rotating angle of the detector 101 is adjusted by controlling the detector rotating motor 103.

A rotating angle of the collimator 202 is adjusted by controlling the tube rotating motor 207.

The above-mentioned rotating angle, traveling distance and vertical moving distance of the elements are controlled by the control unit (not shown).

FIG. 7 is a perspective view showing the case where the chest imaging mode according to the present invention has been selected using the control unit (not shown).

When the control unit (not shown) selects the chest imaging mode, the detector stand 115 and the tube stand 210 are moved to predetermined positions by the rotating force of the detector stand moving motor 304 and the tube stand moving motor 301 in the state in which a distance between the detector stand 115 and the tube stand 210 is maintained constant. In addition, the tube arm 206 and the detector arm 105 are moved to heights corresponding to the chest of the patient by rotating the detector lift motor 108 and the tube lift motor 220 under the control of the control unit (not shown).

Simultaneously, the detector 101 and the collimator 202 are oriented by rotation of the detector rotating motor 103 and the tube rotating motor 207 such that they face each other.

X-rays generated from the X-ray tube 201 is radiated from the X-ray generating unit 200 while the radiating range thereof is controlled by the collimator 202. The radiated X-rays pass through the patient and enter the detector 101. The X-rays absorbed into the detector 101 are converted into data. The data is transmitted to the control unit (not shown), and it is output through an output unit (not shown) after being processed.

FIG. 8 is a perspective view showing the case where table mode according to the present invention has been selected using the control unit (not shown).

When the control unit (not shown) is in table mode, the detector stand 115 and the tube stand 210 are moved to positions where contact is made therebetween by the rotating force of the detector stand moving motor 304 and the tube stand moving motor 301.

Furthermore, according to a control signal of the control unit (not shown), the tube arm 206 is moved to the upper end of the tube stand 210 by the rotating force of the tube lift motor 220 and, simultaneously, the detector arm 105 is moved to the lower end of the detector stand 115 by the rotating force of the detector lift motor 108.

In addition, the detector 101 and the collimator 202 are oriented such that they face each other by rotating the detector rotating motor 103 and the tube rotating motor 207 under the control of the control unit (not shown).

Here, because the detector arm 105 has a bent structure, the center of the detector 101 can be exactly aligned with the center of the collimator 202.

Subsequently, a table (not shown) which is penetrable by X-rays is disposed between the detector 101 and the collimator 202, and the patient is seated on the table.

At this time, a coupling part provided in the table (not shown) is coupled to a table fastener 116 provided on the detector stand 115, so that the table can be reliably supported by the detector stand 115.

In this state, X-rays generated from the X-ray tube 201 are radiated from the X-ray generating unit 200 while the radiating range thereof is controlled by the collimator 202. The radiated X-rays pass through the patient and enter the detector 101. The X-rays absorbed into the detector 101 are converted into data. The data is transmitted to the control unit (not shown) and output through the output unit (not shown) after being processed.

In the rail system and the X-ray imaging apparatus using the rail system according to the present invention having the above-mentioned construction and operation, because the rail is provided only at the one lower side, a sufficiently large space for installation or movement of the table can be ensured. Therefore, for example, if the patient is having an emergency, a table (not shown) on which the patient is lying can be directly disposed between the detector 101 and the collimator 202 to rapidly image the patient.

In table mode, the required distance between the detector 101 and the collimator 202 for imaging using X-rays is 1000 mm. Therefore, it is preferable that the detector stand 115 and the tube stand 210 be designed such that each has a height ranging from 100 mm to 1300 mm. Thanks to this design, the rail system and the X-ray imaging apparatus according to the present invention can be used, for example, even in a hospital having a relatively low ceiling, that is, a small installation space.

Figure 9:
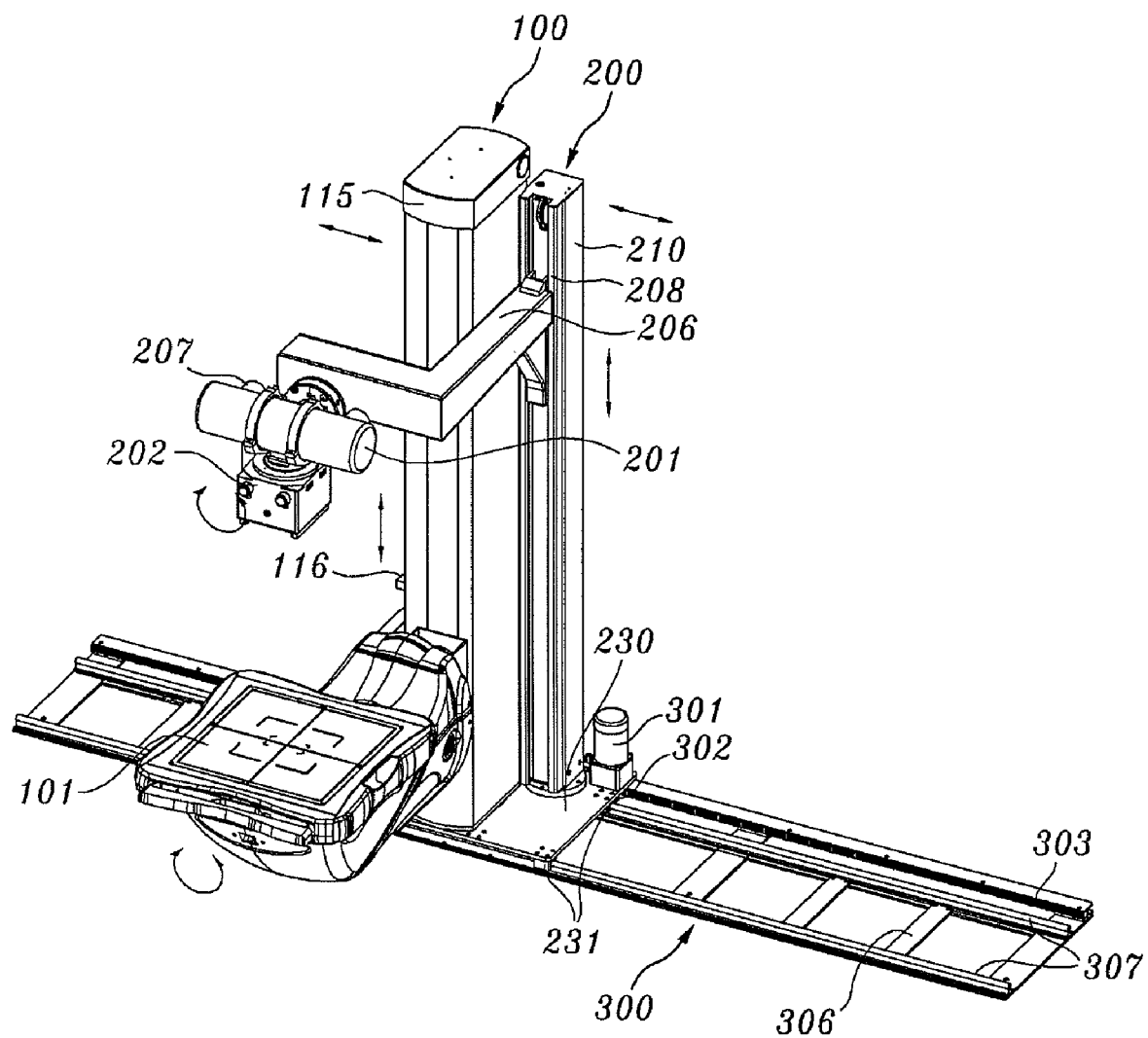
FIG. 9 is a perspective view illustrating a rail system, provided with a tube arm having a bent structure, and an X-ray imaging apparatus using the rail system, according to a second embodiment of the present invention.

FIG. 9 is a perspective view illustrating a rail system, provided with a tube arm having a bent structure, and an X-ray imaging apparatus using the rail system, according to a second embodiment of the present invention.

In the following description of the rail system and the X-ray imaging apparatus according to the second embodiment of the present invention, the description pertaining to the same elements as those of the rail system and the X-ray imaging apparatus according to the first embodiment will be skipped, and only elements different therefrom will be explained.

In the second embodiment, a detector arm 105 is provided on a front surface of a detector stand 115 so as to be movable upwards and downwards.

The tube arm 206 having the bent structure is coupled to the tube stand 210 so as to be movable upwards and downwards such that the distal end of the tube arm 206 faces a detecting unit 100.

The operation of the rail system, provided with the tube arm 206 having the bent structure, and the X-ray imaging apparatus using the rail system according to the present invention will be explained below.

The operation of the second embodiment when the control unit (not shown) is in chest imaging mode is the same as that of the first embodiment and therefore further explanation of it is deemed unnecessary.

The operation of the second embodiment when the control unit (not shown) is in table mode will be explained in detail below.

When table mode has been selected in the control unit (not shown), the detector stand 115 and the tube stand 210 are moved to positions coming into contact with each other by the rotating force of the detector stand moving motor 304 and the tube stand moving motor 301.

Furthermore, according to a control signal of the control unit (not shown), the tube arm 206 is moved to the upper end of the tube stand 210 by the rotating force of the tube lift motor 220 and, simultaneously, the detector arm 105 is moved to the lower end of the detector stand 115 by the rotating force of the detector lift motor 108.

In addition, the detector 101 and the collimator 202 are oriented such that they face each other by the rotating force of the detector rotating motor 103 and the tube rotating motor 207.

Here, because of the tube arm 206 having the bent structure, the center of the detector 101 can be exactly aligned with the center of the collimator 202.

Subsequently, a table (not shown) which allows penetration of X-rays is disposed between the detector 101 and the collimator 202, and the patient is seated on the table.

At this time, a coupling part provided in the table (not shown) is coupled to a table fastener 116 provided on the detector stand 115, so that the table can be reliably supported by the detector stand 115.

In this state, X-rays generated from the X-ray tube 201 are radiated from the X-ray generating unit 200 while the radiating range thereof is controlled by the collimator 202. The radiated X-rays pass through the patient and enter the detector 101. The X-rays absorbed into the detector 101 are converted into data. The data is transmitted to the control unit (not shown), and it is output through the output unit (not shown) after being processed.

In the rail system and the X-ray imaging apparatus using the rail system according to the present invention having the above-mentioned construction and operation, because the rail is provided only at the one lower side, a sufficiently large space for installation or movement of the table can be ensured. Therefore, for example, if the patient is having an emergency, the table (not shown) on which the patient is lying can be directly disposed between the detector 101 and the collimator 202 to rapidly image the patient.

In table mode, the distance required between the detector 101 and the collimator 202 for imaging using X-rays is 1000 mm. Therefore, it is preferable that the detector stand 115 and the tube stand 210 be designed such that each has a height ranging from 100 mm to 1300 mm. Thanks to this design, the rail system and the X-ray imaging apparatus according to the present invention can be used, for example, even in a hospital having a relatively low ceiling, that is, a small installation space.

Figure 10:
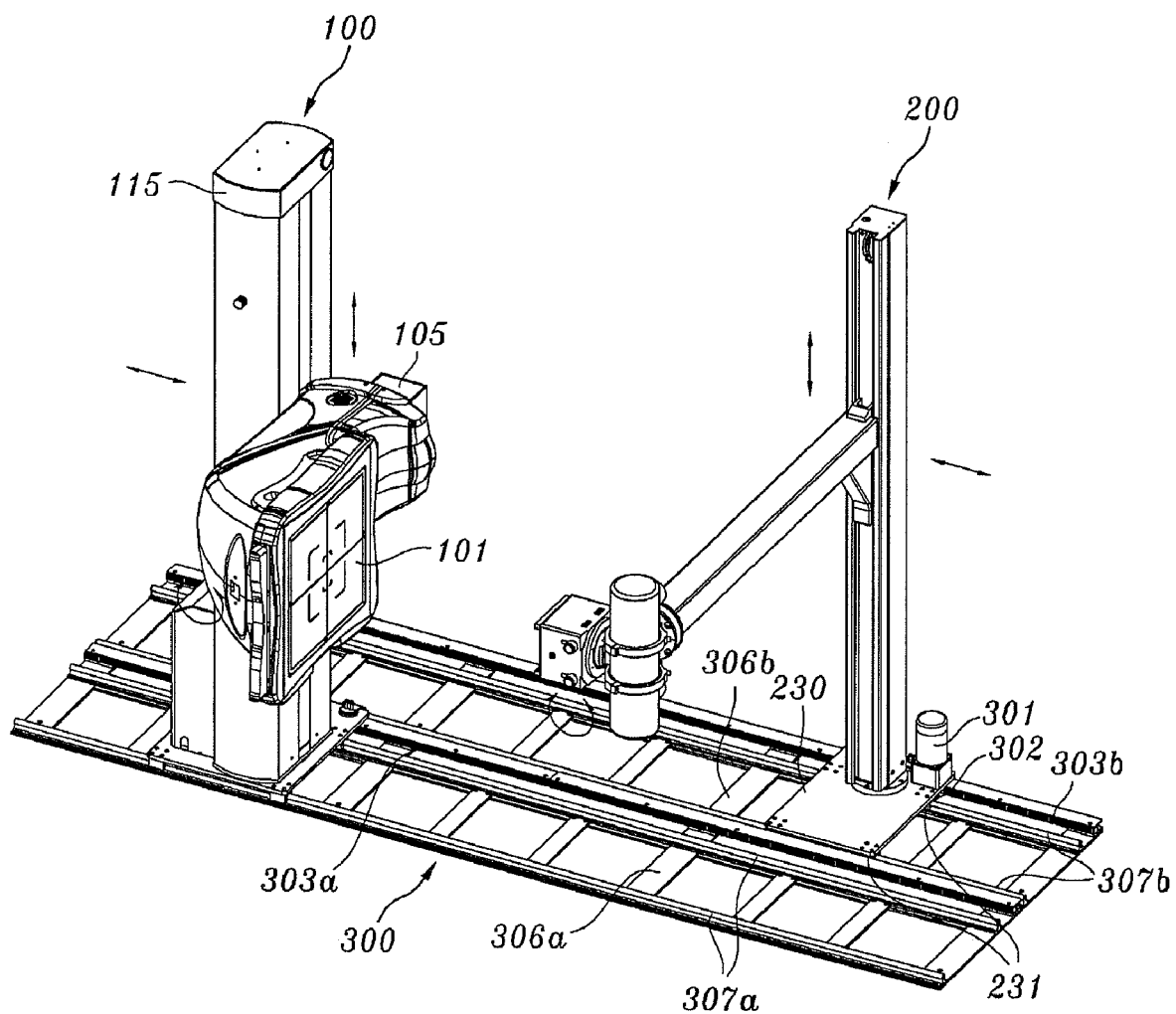
FIG. 10 is a perspective view illustrating a rail system, provided with two rails and a detector arm having a bent structure, and an X-ray imaging apparatus using the rail system, according to a third embodiment of the present invention.

FIG. 10 is a perspective view illustrating a rail system, provided with two rails and a detector arm having a bent structure, and an X-ray imaging apparatus using the rail system, according to a third embodiment of the present invention.

As shown in FIG. 10, a detecting unit 100 provided the detector arm 105 having the bent structure may be provided on a first rail 306a, and an X-ray generating unit 200 may be provided on a second rail 306b.

Alternatively, a detecting unit 100 may be provided on the first rail 306a, and an X-ray generating unit 200 provided with a tube arm 206 having a bent structure may be provided on the second rail 306b.

The operation of the rail system having the two rails and the X-ray imaging apparatus using this rail system according to the third embodiment of the present invention is the same as that of the rail system having the single rail and the X-ray imaging apparatus using this rail system according to the first or second embodiment of the present invention, therefore further explanation is deemed unnecessary.

As described above, in a rail system and an x-ray imaging apparatus using the rail system according to the present invention, because a detector and an X-ray generating unit move along a single rail, space for movement of a table on which a patient is lying for X-ray imaging can be sufficiently ensured.

Furthermore, a table fastener is provided on a detector stand, so that the table can be reliably fastened to the X-ray imaging apparatus.

In addition, in the present invention, the detector arm or the tube arm has a bent structure. Therefore, even when the distance required between the detector and the X-ray generating unit when imaging a patient who is lying on the table is taken into account, the heights of the detector stand and the tube stand can be reduced.

Although the rail system and the X-ray imaging apparatus using the rail system according to the present invention has been disclosed for illustrative purposes, those skilled in the art will appreciate that various modifications, additions and substitutions are possible, without departing from the scope and spirit of the invention as disclosed in the accompanying claims.

What is claimed is:

1. A rail system for X-ray imaging apparatuses, comprising:
   a rail unit provided on a support surface and extending a first predetermined length in a longitudinal direction, the rail unit including:
      a rail supported on the support surface and extending a second predetermined length,
      a rail guide provided along an entire length of the rail, and
      a rack gear provided along the entire length of the rail;
   a detecting unit provided on the rail unit, the detecting unit including:
      a detector stand provided on the rail unit so as to be movable in the longitudinal direction of the rail unit,
      a detector arm coupled to a side surface of the detector stand so as to be movable upwards and downwards, the detector arm having a bent structure,
      a detector coupled to the detector arm, the detector being rotatable with respect to the detector arm,
      a detector support plate having under a lower surface thereof a guide block movably fitted over the rail guide,
      a detector stand moving motor provided on the detector support plate to provide drive force for moving the detector support plate with respect to the rail in the longitudinal direction of the rail,
      a detecting unit pinion gear provided on an output shaft of the detector stand moving motor, the detecting unit pinion gear engaging with the rack gear of the rail unit,
      a detector lift motor provided on the detector support plate to provide drive force for moving the detector support plate upwards and downwards,
      a lower chain pulley coupled to an output shaft of the detector lift motor through a detecting unit belt,
      the detector stand placed upright on the detector support plate,
      a chain engaging with the lower chain pulley, the chain provided to move over an entire range within which the detector moves upwards and downwards,
      an upper chain pulley provided on an upper end of the detector stand so as to be rotatable, the upper chain pulley engaging with the chain,
      a detector guide rail mounted to the detector stand, the detector guide rail extending a third predetermined length in a vertical direction of the detector stand,
      an arm assembly coupled on an inner surface thereof to the chain, the arm assembly movably fitted over the detector guide rail,
      a detector rotating motor provided on the detector arm, and
      a detector mounting plate coupled to an output shaft of the detector rotating motor through a worm gear engagement structure so as to be rotatable; and
   an X-ray generating unit provided on the rail unit at a position facing the detector, the X-ray generating unit including:
      a tube stand provided on the rail unit so as to be movable in the longitudinal direction of the rail unit,
      a tube arm provided on the tube stand so as to be movable upwards and downwards,
      an X-ray tube coupled to the tube arm so as to be rotatable with respect to the tube arm, and
      a collimator fastened to the X-ray tube,
   wherein the detector arm of the detecting unit is fastened to a surface of the arm assembly facing the X-ray generating unit and the detector is fastened to the detector mounting plate, so that the detector is rotatable with respect to the detector arm.

2. The rail system as set forth in claim 1, wherein the X-ray generating unit comprises:
   a tube stand support plate having under a lower surface thereof a guide block movably fitted over the rail guide;
   a tube stand moving motor provided on the tube stand support plate to provide drive force for moving the tube stand support plate with respect to the rail in the longitudinal direction of the rail;
   an X-ray generating unit pinion gear provided on an output shaft of the tube stand moving motor, the X-ray generating unit pinion gear engaging with the rack gear of the rail unit;
   the tube stand placed upright on the tube stand support plate;
   a tube lift motor provided in an upper end of the tube stand;
   a pulley shaft connected to an output shaft of the tube lift motor by a X-ray generating unit belt, so that the pulley shaft is rotated by rotation of the output shaft of the tube lift motor;
   a pulley fitted over the pulley shaft;
   a tube stand wire provided in the tube stand, the tube stand wire being connected to the pulley;
   a tube guide rail mounted to the tube stand, the tube guide rail extending a fourth predetermined length in a vertical direction of the tube stand;
   the tube arm movably coupled to the tube guide rail, the tube arm being connected to the tube stand wire so that the tube arm is moved upwards and downwards by movement of the tube stand wire;
   a tube rotating motor provided on a distal end of the tube arm;
   a rotating plate fastened to an output shaft of the tube rotating motor;
   the X-ray tube coupled to the rotating plate, so that the X-ray tube is rotated along with the rotating plate; and
   the collimator fastened to the X-ray tube to control an X-ray radiation dispersal range.

3. The rail system as set forth in claim 1, wherein the detector stand further comprises a table fastener.

4. An X-ray imaging apparatus using the rail system of claim 1.

* * * * *